(12) United States Patent
Thornton et al.

(10) Patent No.: US 9,101,680 B2
(45) Date of Patent: Aug. 11, 2015

(54) ABSORBENT ARTICLE WITH LOTION

(75) Inventors: Mark Andrew Thornton, Oberursel (DE); Cornelia Beate Martynus, Nidderau-Ostheim (DE); Ekaterina Anatolyevna Ponomarenko, Bad Soden (DE); Victor Nicholas Vega, Cincinnati, OH (US); Brandon Ellis Wise, Cincinnati, OH (US); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 331 days.

(21) Appl. No.: 12/121,375

(22) Filed: May 15, 2008

(65) Prior Publication Data

US 2008/0287900 A1 Nov. 20, 2008

Related U.S. Application Data

(63) Continuation-in-part of application No. 11/946,631, filed on Nov. 28, 2007, now abandoned.

(30) Foreign Application Priority Data

May 15, 2007 (EP) .................................. 07108199
May 15, 2007 (EP) .................................. 07108202

(51) Int. Cl.
*A61F 13/15* (2006.01)
*A61F 13/20* (2006.01)
(Continued)

(52) U.S. Cl.
CPC *A61L 15/16* (2013.01); *A61L 15/50* (2013.01)

(58) Field of Classification Search
CPC ......... A61F 13/15; A61F 13/20; A01N 25/34; A61L 9/00
USPC ................... 604/359–61, 364, 367, 378, 382, 604/385.01, 385.08, 385.09, 385.06, 604/385.13, 385.19, 385.201, 385.24–385.3
See application file for complete search history.

(56) References Cited

U.S. PATENT DOCUMENTS

| 1,926,900 A | 9/1933 | Haas |
| 1,946,911 A | 2/1934 | Lindberg et al. |

(Continued)

FOREIGN PATENT DOCUMENTS

| CN | 1555274 A | 12/2004 |
| EP | 1371379 A1 | 12/2003 |

(Continued)

OTHER PUBLICATIONS

EP Opinion for Application No. EP 07 108 199.6.
(Continued)

*Primary Examiner* — Tatyana Zalukaeva
*Assistant Examiner* — Benedict L Hanrahan
(74) *Attorney, Agent, or Firm* — Laura L. Whitmer; Richard L. Alexander (57) ABSTRACT

An absorbent article to be worn by a wearer having a skin-contacting sheet such as a topsheet, a backsheet, an absorbent core and a colored hydrophilic lotion, that not only helps to reduce the adherence of the menses or feces to the skin, thereby improving the ease of menses or bowl movement (BM) clean up, but that also may serve as a wetness indicator. The absorbent articles may be infant (baby) diapers, including training pants, adult incontinence articles and the like.

9 Claims, 2 Drawing Sheets

(51) Int. Cl.
*A61L 15/16* (2006.01)
*A61L 15/50* (2006.01)

(56) References Cited

U.S. PATENT DOCUMENTS

| | | | |
|---|---|---|---|
| 3,322,123 A | 5/1967 | Griswold et al. | |
| 3,489,148 A | 1/1970 | Duncan et al. | |
| 3,860,003 A | 1/1975 | Buell | |
| 4,022,211 A * | 5/1977 | Timmons et al. | 604/361 |
| 4,253,461 A | 3/1981 | Strickland et al. | |
| 4,597,760 A | 7/1986 | Buell | |
| 4,597,761 A | 7/1986 | Buell | |
| 4,695,278 A | 9/1987 | Lawson | |
| 4,704,115 A | 11/1987 | Buell | |
| 4,738,676 A | 4/1988 | Osborn, III | |
| 4,738,678 A | 4/1988 | Paulis | |
| 4,795,454 A | 1/1989 | Dragoo | |
| 4,804,909 A | 2/1989 | Fink | |
| 4,808,178 A | 2/1989 | Aziz et al. | |
| 4,909,802 A | 3/1990 | Ahr et al. | |
| 4,964,860 A | 10/1990 | Gipson et al. | |
| 5,151,092 A | 9/1992 | Buell et al. | |
| 5,176,672 A * | 1/1993 | Bruemmer et al. | 604/385.19 |
| 5,221,274 A | 6/1993 | Buell et al. | |
| 5,246,433 A | 9/1993 | Hasse et al. | |
| 5,261,531 A | 11/1993 | Nieves | |
| 5,318,774 A * | 6/1994 | Alban et al. | 424/59 |
| 5,482,765 A | 1/1996 | Bradley et al. | |
| 5,509,915 A * | 4/1996 | Hanson et al. | 604/378 |
| 5,525,346 A | 6/1996 | Hartung et al. | |
| 5,554,145 A | 9/1996 | Roe et al. | |
| 5,607,760 A | 3/1997 | Roe | |
| 5,609,587 A | 3/1997 | Roe | |
| 5,643,588 A | 7/1997 | Roe et al. | |
| 5,762,644 A | 6/1998 | Osborn, III et al. | |
| 5,827,917 A * | 10/1998 | Fourty | 524/451 |
| 5,830,487 A * | 11/1998 | Klofta et al. | 424/402 |
| D404,814 S | 1/1999 | Mayer | |
| 5,965,508 A * | 10/1999 | Ospinal et al. | 510/355 |
| 5,965,805 A | 10/1999 | Watts et al. | |
| 5,968,025 A | 10/1999 | Roe et al. | |
| 5,968,528 A * | 10/1999 | Deckner et al. | 424/401 |
| 6,042,842 A * | 3/2000 | Lemann et al. | 424/401 |
| 6,107,537 A | 8/2000 | Elder et al. | |
| 6,120,488 A | 9/2000 | Vanruswijck et al. | |
| 6,120,783 A | 9/2000 | Roe et al. | |
| 6,153,209 A * | 11/2000 | Vega et al. | 424/404 |
| 6,166,285 A | 12/2000 | Vanruswijck et al. | |
| 6,217,890 B1 | 4/2001 | Paul et al. | |
| 6,270,486 B1 | 8/2001 | Brown et al. | |
| 6,270,487 B1 | 8/2001 | Sheehan et al. | |
| 6,290,979 B1 | 9/2001 | Roe et al. | |
| 6,315,806 B1 | 11/2001 | Torobin et al. | |
| H2013 H | 2/2002 | Boyd et al. | |
| 6,372,202 B1 * | 4/2002 | Simon | 424/63 |
| 6,403,107 B1 * | 6/2002 | Lemann | 424/401 |
| 6,426,444 B2 * | 7/2002 | Roe et al. | 604/364 |
| 6,475,197 B1 | 11/2002 | Krzysik et al. | |
| 6,476,288 B1 | 11/2002 | Vanrijswijck et al. | |
| 6,482,191 B1 | 11/2002 | Roe et al. | |
| 6,515,029 B1 | 2/2003 | Krzysik et al. | |
| 6,570,054 B1 | 5/2003 | Gatto et al. | |
| 6,570,055 B2 | 5/2003 | Yang et al. | |
| 6,689,932 B2 | 2/2004 | Kruchoski et al. | |
| 6,695,992 B2 | 2/2004 | Reneker | |
| 6,743,965 B2 | 6/2004 | Yang et al. | |
| 6,749,860 B2 | 6/2004 | Tyrrell et al. | |
| 6,756,520 B1 | 6/2004 | Krzysik et al. | |
| 6,861,571 B1 * | 3/2005 | Roe et al. | 604/364 |
| 7,158,269 B2 | 1/2007 | Morita | |
| 7,223,261 B2 | 5/2007 | Müeller et al. | |
| 7,273,476 B2 | 9/2007 | Mueller et al. | |
| 7,771,735 B2 | 8/2010 | Dvoracek et al. | |
| 7,781,641 B2 | 8/2010 | Kasai | |
| 2002/0016579 A1 | 2/2002 | Stenberg | |
| 2002/0120241 A1 | 8/2002 | Tyrrell et al. | |
| 2002/0123731 A1 | 9/2002 | Yang et al. | |
| 2003/0130636 A1 | 7/2003 | Brock et al. | |
| 2003/0154904 A1 | 8/2003 | Klofta et al. | |
| 2004/0092900 A1 | 5/2004 | Hoffman et al. | |
| 2004/0092901 A1 | 5/2004 | Reece et al. | |
| 2004/0092902 A1 | 5/2004 | Hoffman et al. | |
| 2004/0162538 A1 | 8/2004 | Mueller et al. | |
| 2004/0266300 A1 | 12/2004 | Isele et al. | |
| 2005/0008776 A1 | 1/2005 | Chhabra et al. | |
| 2005/0058669 A1 | 3/2005 | Krzysik et al. | |
| 2005/0059941 A1 | 3/2005 | Baldwin et al. | |
| 2005/0095942 A1 | 5/2005 | Mueller et al. | |
| 2005/0101927 A1 | 5/2005 | Joseph et al. | |
| 2005/0129651 A1 * | 6/2005 | Gatto et al. | 424/70.13 |
| 2005/0177123 A1 | 8/2005 | Catalan | |
| 2005/0256476 A1 | 11/2005 | Mirle et al. | |
| 2005/0261648 A1 | 11/2005 | Mirle et al. | |
| 2005/0276865 A1 * | 12/2005 | Buyuktimkin et al. | 424/616 |
| 2006/0014460 A1 | 1/2006 | Isele et al. | |
| 2006/0025737 A1 | 2/2006 | Song et al. | |
| 2006/0045890 A1 | 3/2006 | Gonzalez et al. | |
| 2006/0057922 A1 | 3/2006 | Bond et al. | |
| 2006/0058765 A1 | 3/2006 | Mueller et al. | |
| 2006/0058766 A1 | 3/2006 | Mueller et al. | |
| 2006/0140924 A1 | 6/2006 | Schroeder et al. | |
| 2007/0286893 A1 | 12/2007 | Marsh et al. | |
| 2008/0286224 A1 | 11/2008 | Vega et al. | |
| 2008/0286320 A1 | 11/2008 | Vega et al. | |
| 2008/0287896 A1 | 11/2008 | Vega et al. | |
| 2009/0137556 A1 * | 5/2009 | Bonnichsen | 514/212.07 |

FOREIGN PATENT DOCUMENTS

| | | |
|---|---|---|
| EP | 1444970 A1 | 8/2004 |
| EP | 1173231 B1 | 8/2005 |
| GB | 2263720 A | 8/1993 |
| JP | 60-186965 | 4/1987 |
| JP | 10-509896 T | 9/1998 |
| JP | 2001-204761 A | 7/2001 |
| JP | 2002-113039 A | 4/2002 |
| JP | 2002-519119 T | 7/2002 |
| JP | 02-084057 | 12/2004 |
| JP | 2006-515573 T | 6/2006 |
| JP | 2006-297071 | 11/2006 |
| WO | WO-92/11830 A2 | 7/1992 |
| WO | WO 96/16682 | 6/1996 |
| WO | WO-97/05908 A2 | 2/1997 |
| WO | WO-97/05909 A2 | 2/1997 |
| WO | WO-98/29078 A1 | 7/1998 |
| WO | WO 99/24010 A1 | 5/1999 |
| WO | WO 99/25288 | 5/1999 |
| WO | WO 9924010 A1 * | 5/1999 |
| WO | WO-99/45973 A1 | 9/1999 |
| WO | WO00/57843 | 10/2000 |
| WO | WO 00/57843 | 10/2000 |
| WO | WO-00/64500 A1 | 11/2000 |
| WO | WO 00/64501 A1 | 11/2000 |
| WO | WO-00/64503 A1 | 11/2000 |
| WO | WO-00/74740 A1 | 12/2000 |
| WO | WO-02/34305 A2 | 5/2002 |
| WO | WO-02/49686 A2 | 6/2002 |
| WO | WO-02/70026 A1 | 9/2002 |
| WO | WO03/028776 | 4/2003 |
| WO | WO-03/057263 A1 | 7/2003 |
| WO | WO 2004/022115 A1 | 3/2004 |
| WO | WO 2005/035011 A1 | 4/2005 |
| WO | WO-2005/035013 A1 | 4/2005 |
| WO | WO 2005/103354 | 11/2005 |
| WO | WO 2005/112854 A1 | 12/2005 |
| WO | WO-2006/022960 A1 | 3/2006 |
| WO | WO 2007/044569 A2 | 4/2007 |

(56) References Cited

FOREIGN PATENT DOCUMENTS

| WO | WO 2007/105147 | 9/2007 |
| WO | WO2007/105147 | 9/2007 |

OTHER PUBLICATIONS

EP Search Report for Application No. EP 07 10 8199, with Annex.

International Search Report, PCT/IB2008/051923, mail date Aug. 13, 2008.
PCT International Search Report, PCT/IB2008/051921 dated May 15, 2008.
All Office Actions, U.S. Appl. No. 12/121,261.
All Office Actions, U.S. Appl. No. 12/121,174.
All Office Actions, U.S. Appl. No. 11/946,631.

\* cited by examiner

ABSORBENT ARTICLE WITH LOTION

CROSS REFERENCE TO RELATED APPLICATION

This application claims priority to EPO Patent Application 07108199.6, filed May 15, 2007; EPO Patent Application 07108202.8, filed May 15, 2007; and U.S. patent application Ser. No. 11/946,631, filed May 15, 2007, the substances of which are incorporated herein by reference.

FIELD OF THE INVENTION

This invention is directed to an absorbent article to be worn by a wearer comprising a feces or menses storage element and comprising a hydrophilic lotion composition, having a water solubility of at least 40% or being a specific hydrophilic lotion as described herein. The feces or menses storage element may be a topsheet with one or more (two-dimensional) openings, and/or a transverse barrier attached to a support structure, for example a pair of cuffs or it may be structure such as an absorbent core comprising one or more (three-dimensional) holes. The lotion composition may be present in, or on this element, and/or in or on another component of the article, which in use is in contact with the skin of the user. Absorbent articles may be infant (baby and toddler) diapers, including training pants; adult incontinence articles; feminine hygiene articles and the like.

BACKGROUND OF THE INVENTION

Disposable absorbent products, such as diapers and sanitary napkins, with a topsheet comprising a lotion are known in the art, for example to deliver skin benefits to the skin of the wearer. In recent years the focus has been to deliver lotions to sanitary napkins and diapers that provide extra skin benefits, for example by addition of botanical ingredients or pharmaceutical ingredients to the lotions. Lotions of various types are known to provide various skin benefits, such as prevention or treatment of diaper rash. These lotions can be applied to the topsheet of absorbent articles, and can be transferred to the skin of the wearer during use. U.S. Pat. No. 5,968,025 to Roe et al., WO 97/05908, WO 97/05909 and US 2006/140924 describe absorbent articles having lotioned topsheets for reducing adherence of BM to the skin, wherein the lotion compositions are primarily hydrophobic. U.S. Pat. No. 3,489, 148 to Duncan et al. teaches a diaper comprising a hydrophobic and oleophobic topsheet wherein a portion of the topsheet is coated with a discontinuous film of oleaginous material. However, in diapers disclosed in the Duncan et al. reference and other diapers treated with hydrophobic lotions, the hydrophobic and oleophobic topsheets are relatively slow in promoting transfer of urine to the underlying absorbent cores.

Separately, absorbent products have been developed over the last decade at least that provide a means to store feces or menses, said means being such that not only the feces or menses is stored, but also kept away from the skin, so that as little as possible contact between the feces or menses and the skin remains. Examples of such means include anal or vaginal cuffs, including topsheets with one or more openings leading to a void space there underneath, to store the feces or menses, said topsheets often being elasticated to form such a void space; structures comprising a transverse barrier to separate the front and the back of the article, to reduce soiling of the genitals with feces; absorbent cores with holes or cavities to store feces or menses etc.

However, there is still a risk that some feces or menses is not stored away in these type of articles, or that complete contact between feces and menses cannot be avoided in use, for example due to extensive soiling, or misplacement of the absorbent article.

Hence, there is still a need to ensure that soiling of the skin by menses or feces is further reduced or eliminated when such products having a feces or menses storage element are used.

It has been found that when a specific hydrophilic lotion composition is provided, a reduction of the adherences of bodily exudates to the skin of the wearer can be achieved. It has been found that the selected hydrophilic lotions herein can be effectively applied to for example the feces or menses storage element so that any feces or menses accidentally not stored in the element, and hence contacting the skin, is easier removed from the skin.

Furthermore, it has been observed that oil-containing hydrophobic lotions used by the care taker or user on the skin of the user or proposed in the art to be sued on absorbent articles can degrade any elastic materials comprised by an absorbent article, such as present in the cuffs, reducing the elastic performance of the article in use.

Surprisingly, the inventors found that the selected hydrophilic lotion compositions of the invention, unlike the hydrophobic lotions known in the art, are much better compatible with elastic materials, so the elastic performance of the article is not affected by said lotions. So, the hydrophilic lotions of the invention can be applied directly to components of the absorbent articles that comprise elastic material, such as the cuffs or an elasticated topsheet, as described herein after) or an elasticated transverse barrier, described herein after.

Furthermore, when the present absorbent article with the specific lotion composition is used, the use of a separate oily lotion or cream by the user or care taker may no longer be needed, reducing thus the risk of elastic degradation of the elastics of the article.

SUMMARY OF THE INVENTION

Embodiments disclosed herein include an absorbent article to be worn by a wearer against the skin. The absorbent articles comprises a backsheet; a feces or menses storage element; and a hydrophilic lotion composition. The hydrophilic lotion composition has a water solubility of at least 40%. The hydrophilic lotion composition comprises 25% to 75% by weight of a first component which is liquid at 25° C., and 25% to 75% by weight of a second component which is solid at 25° C. The first component comprises one or more compounds selected from the group consisting of liquid nonionic surfactants having an HLB value greater than or equal to 10, liquid polyhydric alcoholic solvents, and liquid fatty acid esters comprising at least one fatty acid unit and at least one (poly) ethylene glycol unit and/or (poly) propylene glycol unit. The second component comprises one or more compounds selected from the group consisting of solid polypropylene glycols, solid polypropylene glycol derivatives, solid ethoxylated natural oils, solid ethoxylated natural fats, solid propoxylated natural oils, and solid propoxylated natural fats.

Embodiments disclosed herein also include an absorbent article comprising a backsheet and a feces or menses storage element. The storage element comprises a wearer's skin-faceable surface and a lotion composition. The lotion composition comprises 25% to 75% by weight of a first component which is liquid at 25° C. and 25% to 75% by weight of a second component which is solid at 25° C. The first component comprises one or more compounds selected from the group consisting of: (a) liquid nonionic surfactants having an HLB value greater than or equal to 10; and (b) liquid fatty acid esters comprising at least one fatty acid unit and at least one (poly) ethylene glycol unit and/or (poly) propylene glycol unit. The second component comprises one or more compounds selected from the group consisting of: (c) solid polyethylene glycols, solid polypropylene glycols, solid polyethylene glycol derivatives, or solid polypropylene glycol derivatives; (d) solid nonionic surfactants with HLB value of at least 10; (e) solid fatty compounds selected from the group consisting of solid fatty acids, solid fatty soaps, and solid fatty alcohols; and (f) solid ethoxylated natural oils and fats and propoxylated natural oils and fats.

DETAILED DESCRIPTION OF THE INVENTION

As used herein, the following terms have the following meanings:

Herein, "comprise" and "include" mean that other elements and/or other steps which do not affect the end result can be added. Each of these terms encompasses the terms "consisting of" and "consisting essentially of".

Herein, "body facing surface" refers to surfaces of absorbent articles and/or their component materials which face the body of the wearer, while "garment facing surface" refers to the opposite surfaces of the absorbent articles and/or their component materials that face away from the wearer when the absorbent articles are worn.

Herein, "body" refers to outer layers formed by mammalian epidermal tissues including the skin and hair.

As used herein "absorbent article" refers to devices which are intended to be placed against the skin of a wearer to absorb and contain the various exudates discharged from the body. Absorbent articles of the present invention include diapers, including pant-like diapers, incontinence articles, including e.g. diapers and pads, and feminine hygiene articles, including e.g. sanitary napkins.

As used herein "diaper" refers to an absorbent article generally worn by infants (e.g. babies or toddlers) about the lower torso of the wearer. Suitable diapers are disclosed in, e.g., U.S. Pat. No. 3,860,003 issued to Buell on Jan. 14, 1975; U.S. Pat. No. 5,151,092 issued to Buell et al. on Sep. 29, 1992; U.S. Pat. No. 5,221,274 issued to Buell et al. on Jun. 22, 1993; and U.S. Pat. No. 5,554,145 issued to Roe et al. on Sep. 10, 1996. As used herein the term "diaper" also comprises "pant-like diapers": A pant-like diaper refers to an absorbent article having fixed sides and leg openings. Pant-like diapers are placed in position on the wearer by inserting the wearer's legs into the leg openings and sliding the pant-like diaper into position about the wearer's lower torso. Suitable pant-like diapers are disclosed in, e.g., U.S. Pat. No. 5,246,433, issued to Hasse, et al. on Sep. 21, 1993.

As used herein "incontinence article" refers to an absorbent article worn by a wearer, including pads, undergarments, inserts for absorbent articles, capacity boosters for absorbent articles, briefs, and bed pads. Suitable incontinence articles are disclosed in, e.g., U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and PCT Publication No. WO 92/11830 published by Noel, et al. on Jul. 23, 1992.

As used herein "disposable" is used to describe absorbent articles for single use, which are not intended to be laundered, restored or otherwise reused as an absorbent article after a single use.

As used herein, the terms "migrate", "migration", or "migrating" mean a lotion composition moves from one place to another place by way of movement on a material or permeation through an (for example intervening) material, within the article.

As used herein, the term "transfer" when used in the context of a lotion composition, refers to the lotion composition moving from one area of the absorbent article to the skin of the wearer or to another area on the absorbent article not by way of migration but by way of direct contact of the skin or said other area with the lotion composition, such as in a blotting effect.

As used herein, the term "particulate material" refers to a component of the lotion composition that is insoluble or non-molecularly dispersible in the lotion composition prior to applying this lotion composition to the absorbent article and that remains in particulate form when applied to the absorbent article. It includes all type of particulate forms such as granules, beads, spheres, micro-spheres, powders, as known in the art.

The terms "reducing the adherence" and "anti-stick" are used synonymously. This means that less residual bowel movement or blood remains on the skin when compared to an article without anti-stick lotion composition and/or that the adherence of feces or menses to the human skin of a wearer wearing an absorbent article is reduced, e.g. compared to adherence of feces or blood observed when an absorbent article without said lotion composition is worn (typically with repeated use).

Herein, the terms "feces" and "bowl movement" and "BM" are used interchangeably.

As used herein, the term 'void space' is a cavity in the article present in at least the relaxed state, which serves to accept and contain bodily exudates such as fecal material, typically being at least 1 or at least 2 $cm^3$ in relaxed state.

When used herein, 'longitudinal' is the direction running substantially parallel to the maximum linear dimension of the component, typically to the longitudinal axis of the article, and includes directions within 30° of this parallel, when applicable.

The 'lateral' or 'transverse' direction is orthogonal to the longitudinal direction and in the same plan of the majority of the article and the longitudinal axis and includes directions within 30° of the orthogonal, when applicable.

'Extendibility' and 'extendable', when used herein, means that the width or length of the component (in relaxed position) can be increased.

As used herein 'stretched' or stretched state' means that the article or component thereof, e.g. topsheet thereof, is stretched to its maximum length, which is typically determined by the length of a non-elastically extendable component which is part thereof, e.g. the backsheet or the non-elastically extendable material of the topsheet.

As used herein 'relaxed' or 'relaxed state' means the state that no forces are applied to the article or component thereof (other than naturally occurring forces such as gravity), when the article is laid on a horizontal surface, such that the transverse front and back edge are flat on the horizontal surface and the transverse center line 142 or axis is on the horizontal surface.

As used herein, 'elasticated' means typically, that the component consists of or comprises elastic material, which is elastic in at least one direction. 'Non-elasticated' when used herein means that the component does not comprise any elastic material.

As used herein, 'along' means 'at least partially substantially parallel to and adjacent to'. Adjacent includes 'in close proximity with' and 'in contact with'.

The unit of all molecular weights given herein is Daltons.

The present invention relates to an absorbent article to be worn by a wearer against the skin, comprising a backsheet and a feces or menses storage element; and comprising a hydrophilic lotion composition, having a water solubility of at least 30%, or typically at least 40%.

In another embodiment, the invention relates to an absorbent article to be worn by a wearer against the skin comprising a feces or menses storage element, and comprising, for example on or in said storage element, a lotion composition, said lotion composition comprising i) a first component which is liquid at 25° C.; and ii) a second component which is solid at 25° C., and said first component comprising one or more compounds selected from the group consisting of:

(a) liquid polyhydric alcoholic solvents; including a liquid polyethylene glycol, liquid polypropylene glycol, liquid polyethylene glycol derivatives and/or liquid polypropylene glycol derivatives; and (b) liquid fatty acid esters comprising at least one fatty acid unit and at least one (poly) ethylene glycol unit and/or (poly) propylene glycol unit; and said second component comprising one or more compounds selected from the group consisting of (c) solid polyethylene glycols, solid polypropylene glycol, solid polyethylene glycol derivatives, and/or solid liquid polypropylene glycol derivatives;

(d) solid nonionic surfactants with HLB value of at least 10;

(e) solid fatty compounds selected from the group consisting of solid fatty acids, solid fatty soaps and solid fatty alcohols; and (f) solid ethoxylated natural oils and fats and propoxylated natural oils and fats.

The feces or menses storage element may be a topsheet with one or more 2-dimensional openings, leading to a void space there underneath, to thus form a three-dimensional storage element (said topsheet may be an elasticated topsheet—also called an anal or vaginal cuff); and/or the feces or menses storage element may be a three-dimensional layer, such as an absorbent core or part thereof, comprising one or more holes (including blind holes or through holes), that are three-dimensional and suitable for feces or menses storage, as described herein below; and/or the feces or menses storage element may be a transverse barrier, projecting from the plane of the article, e.g. the absorbent core, and supported by a support structure, for example at least a pair cuffs connected to said transverse barrier; and/or the feces storage element may comprise a waist cap, transversely positioned in the back portion of the article, projecting from the plane of the article; and/or the feces or menses storage element may be a pair of cuffs connected to one another in the center region of the article, forming a front and back pocket; or combinations thereof.

In one embodiment, the storage element is a feces storage element and the article is an infant (baby, toddler) diaper, including a training pant, or adult incontinence article, e.g. an adult diaper.

The lotion composition may be present on, or in, part of or all of said storage element, or it may be present on another component of the absorbent article that in use is in contact with the skin of the user, such as a bodyside lines or core coversheet and/or leg cuffs and/or barrier cuffs of the article.

The lotion composition may be present on the whole surface of the storage element, or the whole surface of another component of the absorbent article, or it may be present on part of such a surface, for example as a single stripe, or in for example in the form of a pattern, for example including a multitude of stripes and/or dots, and/or figures.

In one embodiment, the lotion composition is applied on a component (for example one or more of the feces storage elements herein) that comprises elastic material, and optionally, it may be applied on those portions of the component (e.g. feces or menses storage element) where the elastic material is present.

Lotion Compositions of the Present Invention

The lotion composition of the present invention is a hydrophilic lotion, which means in one embodiment herein that is has a water solubility of at least 40% and it may have (an hydrophilicity such that it) has a water solubility of at least 45% or at least 50%, or at least 55% and optionally up to 65% or up to 60% (as determined according to the method as described herein). In one embodiment herein, the lotion composition is as defined in claim 2, and further described herein after. It may then also have a hydrophilicity and/or water-solubility as specified above.

The lotion composition is present in or on a component of the article, or part thereof, for example in or on the feces or menses storage element herein and/or in or on a skin-contacting sheet, for example the bodyside liner or core coversheet and/or cuffs. The lotion composition may be present on such an element or component, or part thereof. It may be that the lotion composition is at least present on the surface of the sheet that in use faces the user, so that it easily transfers to the skin in use. It may be applied to the element or component by any means. "Applying" as used herein means that said element or component, or surface thereof or part thereof, comprises at least a partial layer of the lotion composition on at least part of one of its surfaces so that at least part of the lotion composition may contact the skin of the wearer in use.

The lotion composition herein may be flowable (e.g. liquid) at suitable process conditions, e.g. above 50° C. or above 60° C. or above 80° C. or optionally above 100° C., but solid or semi-solid (or non-fluid) at a temperature of 25° C. The lotion composition of the present invention is typically non-fluid, i.e. solid or more often semisolid at 25° C., i.e. at ambient temperatures, to minimize migration of the lotion composition. By "semisolid" is meant that the lotion composition has a rheology typical of pseudoplastic or plastic fluids. When no shear is applied, the lotion compositions can have the appearance of a solid but can be made to flow as the shear rate is increased. In one embodiment herein, this may be due to the fact that while the lotion composition contains a component being solid at 25° C. it also includes a component being liquid at 25° C. (Each component may itself comprise one or more compounds.) The lotion composition may have a final melting point (more than 95% liquid) above potential "stressful" storage conditions that can be 45° C. or greater.

Semi-solid or solid as used herein means that 1 g of a material (e.g. lotion composition, component or compound thereof), which is placed in the middle of a round glass plate having a diameter of 15 cm, does not run off a glass plate within 1 minute, when the glass plate is tilted at 45°, under conditions of 25° C. and 50% relative humidity.

All components or compounds being either solid or semi-solid (according to the test-method described above) are herein referred to as "solid compound or solid component". All components or compounds being not solid or semi-solid (according to the test-method described above) are herein referred to as "liquid compound or liquid component".

In one embodiment, the lotion composition is such that 3% to 90% by weight is a liquid component at test temperature of 25° C. In one embodiment the lotion according to present invention is such that 10% to 80% by weight, or 20% to 75% by weight, or 30% to 60% by weight, or 40% to 50% by weight is liquid at a test temperature of 25° C. From 25% to 75% or even 30% to 80% can be liquid at body temperature of 37° C.

It may be that at 25° C. said solid component is present at a level of from 10 to 97 wt. % of the lotion composition or from 20 to 80 wt. % or from 30 to 70 wt. %.

In one embodiment, at 25° C. the total amount of liquid compounds or liquid component of the lotion composition is higher than the total amount of solid compounds or component. For example, in one embodiment, the amount of liquid compounds or liquid component is above 50 wt. % or at least 55 wt. % or at least 60 wt. %. When applied to the absorbent article, the lotion compositions of the present invention are transferable to the wearer's skin by normal contact, wearer motion (thus creating friction), and/or body heat.

The amount of lotion composition should typically be such that it effects a reduction of the adherence of feces or menses to the human skin of a wearer wearing an absorbent article compared to the absorbent article without the lotion composition. Without being bound by theory, it is believed that the lotion composition herein may reduce the adhesive force between the soils or exudates and the skin surface because the adhesive forces may be smaller than the cohesive forces within the soils or exudates, thereby allowing the soils or exudates to detach from the skin surface upon application of a shear force (e.g. such as that generated by wiping).

A suitable amount of the lotion composition according to various embodiments of the present invention may be from about 0.015 grams per square meter (gsm) to about 100 gsm, or 1 gsm to about 80 gsm, or 6 gsm to 50 gsm, or 12 gsm to 40 gsm, or 16 to 30 gsm, or for example from 22 to 26 gsm.

Typically, the lotion composition is applied on at least a portion of the topsheet, for example in said amounts described above.

It has surprisingly also been found that it may be beneficial to add particles or beads to the lotion composition, to further reduce the adherence of BM or blood to the skin, in particular particles or beads that are organic compounds with one or more ester, keton or polyalcohol groups or alkoxylated group(s), such as starch or alkoxylated, e.g. ethoxylated, polyethylene; or inorganic compounds, such as talc, silica, clay, mica seracite. Such beads and properties and quantities thereof are further described below.

Exemplary particles or beads are, as also described in the same section below, polypropylene and/or polyethylene (co) polymer particles and polytetrafluoroethylene particles.

Without being bound by theory, it is believed that the addition of such particles or beads may aid to control the water-solubility and hence hydrophilicity of the lotion such that it provides the reduces adherence to the skin whilst not being so hydrophilic that the lotion dissolves into the bodily exudates, such as urine (and thus to avoid that the lotion may be washed of the absorbent article, or into the article). It has been found that it may be beneficial if the particles or beads have a certain hydrophilicity, whilst not being too hydrophilic.

These particles or beads may be added at any level, for example up to 35% by weight, or up to 20% or up to 15% by weight and for example from 0.1% by weight or from 0.5% by weight, or from 3% by weight or from 5% by weight. Exemplary particle sizes, distributions (etc.) are described in detail below. (The particulate material is considered, e.g. for example for determination of the weight level or ratio's herein, part of the solid component (solid at 25° C.).

In one embodiment, the lotion composition comprises i) a first component which is liquid at 25° C.; and ii) a second component which is solid at 25° C., and said first component comprising one or more compounds selected from the group consisting of:

a) liquid polyhydric alcoholic solvents, liquid polyethylene glycol, liquid polypropylene glycol, liquid polyethylene glycol derivatives, and/or liquid polypropylene glycol derivatives; and b) liquid nonionic surfactants with HLB value of at least 10; and c) liquid fatty acid esters comprising at least one fatty acid unit and at least one (poly) ethylene glycol unit and/or (poly) propylene glycol unit; and said second component comprising one or more compounds selected from the group consisting of:

(c) solid polyethylene glycols, solid polypropylene glycol, solid polyethylene glycol derivatives, and/or solid liquid polypropylene glycol derivatives;

(d) solid nonionic surfactants with HLB value of at least 10;

(e) solid fatty compounds selected from the group consisting of solid fatty acids, solid fatty soaps and solid fatty alcohols.

The weight ratio of first liquid to second solid component may, for example, be from 1:32 to 9:1 or from 1:9 to 9:1 or from 2:8 to 8:2 or from 3:7 to 7:3.

The lotion composition may be essentially non-aqueous. Non-aqueous means, that the lotion compositions either contain no water or they contain water only in minor amounts such as less than 5 wt. % or even less than 1 wt. %. However, these amounts refer to the lotion composition at the time when the absorbent article is produced, i.e. to the time the lotion composition is applied onto the absorbent article. The lotion compositions of the present invention may be hygroscopic, and thus may be able to take up a significant amount of water from the surrounding atmosphere, particularly in an environment with high relative humidity. Thus, when the absorbent article has been stored for a relatively long time, such as for example for unfolded for at least 2 months at 50% relative humidity and 25° C., it is possible that the amount of water contained in the lotion composition has increased to be more than 5 wt %.

In one embodiment herein, the hydrophilic lotion may comprises one or more, or two or more of the following compounds, including at least one solid compound and at least one liquid compound:

Liquid Polyhydric Alcoholic Solvents

Liquid polyhydric alcoholic solvents, when used herein, are organic compounds having at least 2 carbon atoms and at least two alcoholic hydroxy groups and which are liquid at 25° C., excluding for the purpose of the invention polyethylene glycols, polypropylene glycols and derivatives, as described herein below, as separate groups. Examples are glycerol, ethylene glycol, diethylene glycol, propylene glycol, butylene glycol, dipropylene glycol, methyl propanediol and derivatives thereof, including for example mono- or di-end capped diethylene glycols, mono- or di-end capped dipropylene glycols, mono- or di-end capped ethylene glycols and mono- or di-end capped propylene glycols, having end-capped units as described above.

Liquid compounds herein include: ethoxylated fatty acids, such as PEG-8 laurate, available for example as Lipopeg 4-L from Lipo Chemicals; ethoxylated fatty ester (oil), such as a PEG-25 castor oil, for example available as hetoxide C-25 from Global-Seven Inc.; Glycerol esters, such as for example a PEG-10 polyglyceryl-2 laurate, available for example as Hostacerin DGL from Clariant Corp.; Lecithin, such as available as Alcolec BS from American Lecithin Co.; polymeric surfactants such as a C8-C10 alkyl polysaccharide ether, available for example as Glucopan 225 DK from Cognis Corp.); Sorbitan derivatives such as POE (20) sorbitan monopalmitate available for example from Croda Inc.; sucrose and glucose esters and derivatives, such as alkyl polyglucoside, available for example as Simulsol AS48 from Seppic Inc.

Liquid Polyethylene Glycols and Derivatives and Liquid Polypropylene Glycol and Derivatives.

Liquid polyethylene glycols and derivatives are liquid at 25° C. The polyethylene glycols (PEG's) are made from at least 3 units of ethylene glycol and have the general formula $$HO-(CH2-O-CH2-O)_x-H$$

with x being a number of from 3 to 15 or from 8 to 12. The molecular weight (weight average) may be from 100 to less than 720 or from 100 or 350 to 700. Typical liquid polyethylene glycols are known as PEG-4, PEG-6, PEG-7, PEG-8, PEG-9, PEG-10, PEG-12 and PEG-14. Suitable trade products are for example Polyglykol 400 of Clariant with an average molecular weight of 380 to 410 or Polyglykol 600 with an average molecular weight of 570 to 630.

Liquid PEG and PPG derivatives may include esters and ethers of PEG and PPG. Liquid derivates of PEG and PPG include in particular PEG's and PPG's (for example as described above) having however one or more (mono or di end capped, respectively) end cap groups, derived from an organic compound capable of reacting with a hydroxyl group. End cap groups include methyl, ethyl, propyl, isopropyl, butyl, isobutyl, tert-butyl and benzyl, for example mono- or di-methyl or -ethyl end capped PEG or PPG. In some embodiment, methyl may be an end-capping unit.

Further polypropylenes and end capping units useful in this invention are described in co-pending application US60/901, 793, filed 16 Feb. 2007.

A liquid mono-end capped PEG may be for example a polyethylene glycol monomethyl ether, such as available as Polyglykol M400 from Clariant Corporation. A liquid PEG includes also a Polyethylene glycol dimethyl ether with a MW of 500 (available from Sigma Aldrich).

Also useful herein are liquid ethylene oxide-propylene oxide copolymers and polyethylene-polypropylene block copolymers (EO-PO block copolymers), such as Genapol PF10—a EO-PO block copolymer from Clariant Corp.)

Liquid Alkylene (e.g. Ethylene) Glycol Fatty Acid Esters

Suitable liquid alkylene or ethylene glycol fatty acid esters may be for example the esters of one or more alkylene glycol units, ethylene glycol units, and one or two fatty acids. These compounds may have the general formula $$R^1-(OCH2CH2)_mO-R^2$$

where $R^1$ and $R^2$ are hydrogen or fatty acid residues with e.g. from 6 to 30 or from 8 to 22 carbon atoms and can be the same or different with the proviso that not both are hydrogen; and m is a number of at least 1. R1 and R2 may be different and m may be 1, 2, or 3. Typical ethylene glycol esters are known for example as diethylene glycol diethylhexanoate/diisononanoate, diethylene glycol diisononanoate, diethylene glycol dilaurate, diethylene glycol dioctanoate/diisononanoate and diethylene glycol distearate. Suitable trade product mixtures containing ethylene glycol esters are for example DERMOL MO or DERMOL 489. Wax esters may be liquid at room temperature (25° C.). They may be derived from natural sources such as jojoba oil, comprising docosenyl eicosenoate, eicosenyl eicosenoate and eicosenyl docosenoate.

Solid Polyethylene Glycol and Polypropylene Glycols and Derivatives Thereof

Solid polyethylene glycols, polypropylene glycols and derivatives thereof are solid (or semi-solid—as defined above) at 25° C., as defined herein. The solid polyethylene glycols are typically made from at least 16 units of ethylene glycol and have the general formula $$HO-(CH2-O-CH2-O)_y-H$$

with y being a number of at least 16, e.g. from 20 to 220 or from 40 to 150. The molecular weight (weight average) is above 720, e.g. from 720 to 100000, or from 950 or 1500 or 2000 or 2700 to 30000. Typical solid polyethylene glycols are known as PEG-20, PEG-32, PEG-40, PEG-45, PEG-55, PEG-60, PEG-75, PEG-90 and PEG-100. Suitable trade products are for example Polyglykol 3000 of Clariant with an average molecular weight of 2700 to 3000 or Polyglykol 4000 with an average molecular weight of 3700 to 4500.

Solid PEG and PPG derivatives may include esters and ether derivates of PEG's and PPG's. Solid derivatives include in particular PEG's and PPG's (for example as described above) having one or more end cap groups (mono or di end capped, respectively), such as those described above.

For example, a solid mono-end capped PEG such as Polyglykol M4000 (polyethylene glycol monomethyl, from Clariant Corporation) may be used and/or a solid di-endcapped PEG such as Polyethylene glycol dimethyl ether MW2000 (from Sigma Aldrich) may be used.

Also useful herein may be solid EO-PO copolymers and EO-PO block copolymers, such as for example Genapol PF80, an EO-PO block copolymer from Clariant Corp.

Solid Nonionic Surfactants

Suitable solid nonionic surfactants with an HLB value of at least 10 include solid PEG derived nonionic surfactants, solid polyalkylene glycol fatty alcohol ethers, such as solid polyethylene glycol fatty alcohol ethers or for example solid polyethoxylated fatty alcohols. The fatty alcohols unit may have from 8 to 30 carbon atoms, or from 12 to 22 carbon atoms. The average degree of alkoxylation, e.g. ethoxylation, may be from 2 to 200, at least 10, at least 20 or at least 30. These surfactants may be nonionic surfactants with HLB values of at least 10, or at least 12 or at least 13, up to for example 17. Polyethylene glycol fatty alcohol ethers have the general formula $$R(OCH2CH2)_nOH$$

where R represents an alkyl group or a blend of alkyl groups with for example 8 to 30 or 12 to 22 carbon atoms and n is the degree of ethoxylation, e.g. 2 to 200. Suitable PEG derived surfactants include PEG-12 stearate, PEG-100 stearate, for example available as Tego Acid S 100 P from Evonik/Degussa.

Suitable trade products include also for example BRIJ 76, BRIJ 78 and BRIJ 700 (Stearteth 100, available from Croda Inc.).

Other surfactants include Ceteraeth-10, Ceteareth-20, Polysorbate-65. Also used may be Laureth 23.

Suitable fatty alcohol fatty acid esters are esters of a C10 to C30 fatty alcohol with a C10- to C30-fatty acid. They have the general formula $R^3$—CO—O—$R^4$ where $R^3$—CO is a C10- to C30 fatty acid residue and O—$R^4$ is a C10- to C30 fatty alcohol residue. They may be saturated or unsaturated.

Other suitable nonionic surfactant are e.g. ethoxylated alcohols, ethoxylated fatty acids, ethoxylated fatty esters and oils, glycerol esters; sucrose and glucose esters and their derivatives, glucosides, sorbitan derivatives, such as sorbitan monoplamitate.

Other compounds include PEG oils, like PEG40 hydrogenated castor oil, PEG-20 sorbitan monooleate, PEG-200 castor oil, available for example as Hetoxide C-200 from Global-Seven Inc.; glycerol esters such as a decaglycerol mono/dioleate, available for example as Caprol PGE860 from Abitec Corp.; lecithin derivatives, such as soy phosphatides, such as available as Alcolec Powder from American Lecithin Co.; sorbitan derivatives, such as Polysorbate 65, such as available as Liposorb TS-20 from Lipo Chemicals; sucrose and glucose esters and derivatives such as succinoglycan, available for example as Rheozan from Rhodia, Inc.

Solid Fatty Compounds:

The solid fatty compounds are selected from the group consisting of: fatty acids, solid fatty soaps and solid fatty alcohols. The solid fatty compounds are solid at (or at least semi-solid according to the method described herein, at 25° C.). The fatty compounds may have from 10 to 30 or from 12 to 22 carbon atoms. The fatty compounds can be saturated or unsaturated and they can be linear or branched. These compounds may be saturated, linear, and fatty. Examples of solid fatty acids are decanoic acid, lauric acid, myristic acid, palmitic acid, stearic acid, arachidic acid or behenic acid. These compounds may be solid fatty alcohols that are linear, unsaturated 1-alkanols with at least 12 carbon atoms. Examples of solid fatty alcohols are lauryl alcohol, myristyl alcohol, cetyl alcohol, stearyl alcohol, arachidyl alcohol or behenyl alcohol.

The solid fatty soaps are metallic soaps which are metal salts of fatty acids. The fatty acid components of the fatty soaps are the same as mentioned above. Suitable metal cations are sodium, potassium, lithium, aluminium, magnesium, calcium, mangan, iron, zirconium, cerium, zinc, cobalt or vanadium. Metallic soaps with low water solubility such as the calcium or magnesium salts, e.g. calcium stearate may be used.

Exemplary Compositions:

It may be that the first liquid component comprises one or more compounds selected from the group consisting of: methoxyisopropanol, propyl ether, dipropylene glycol butyl ether, methyl propanediol, propylene carbonate, ethylene glycols, diethylene glycols, propylene glycols, dipropylene glycols, glycerin, sorbitol, hydrogenated starch hydrolysate, silicone glycols, or any of the above mentioned or exemplified polyethylene glycol or derivatives, polypropylene glycol or derivatives, polyethylene glycol derived surfactants, polypropylene derived surfactants, ethylene glycol or derivatives, propylene glycol or derivatives, diethylene glycol or derivatives and dipropylene glycol or derivatives, as described herein.

The second, solid component may comprise for example one or more solid compounds (as defined above) of the group including: solid polyethylene glycol or derivatives thereof; solid polypropylene glycol or derivatives thereof; solid nonionic surfactants with HLB value of at least 10; solid fatty compounds selected from the group consisting of solid fatty acids, solid fatty soaps and solid fatty alcohols; solid PEG derived surfactants; solid PPG derived surfactants; ethoxylated natural fats or propoxylated natural fats, such as PEG-150 jojoba.

Exemplary lotion compositions may be such that:

said first liquid component may comprise a liquid polyethylene glycol and/or liquid polypropylene glycol and said second component may comprise a solid nonionic surfactant with an HLB value of at least 10, provided that when said solid nonionic surfactant is an alkoxylated (e.g. ethoxylated) fatty alcohol, then the HLB value is at least 13; or said first component may comprise a liquid fatty acid ester comprising at least one fatty acid unit and at least one ethylene glycol unit and said second component may comprise a solid polyethylene glycol; or said first component may comprise a liquid polyethylene glycol and said second compound is a solid fatty compounds selected from the group consisting of solid fatty acids and solid fatty soaps and solid fatty alcohols.

When said solid fatty compound comprises a solid fatty acid, then the total amount of liquids may be higher than the total amount of solids.

In one embodiment the liquid component is a polyethylene glycol having a molecular weight (weight average) of 100 to less than 720, or from 350 to 700. It may be that the lotion composition comprises from 20% to 80% by weight, or 30% to 70% by weight, or 40% to 60% by weight of this liquid polyethylene glycol. For example 50% by weight of polyethylene glycol with a MW of 400, also referred to as Polyglycol 400.

In one embodiment the solid component is a polyethylene glycol or derivative, where appropriate, having a molecular weight (weight average) of above 720, e.g. from 720 to 100000, or from 950 to 30000, or from 3000 to 20000 or to 10000. It may be that the lotion composition comprises from 20% to 80% by weight, or 30% to 70% by weight, or 40% to 60% by weight of this liquid polyethylene glycol, for example 50% by weight of Polyglycol 4000.

In one embodiment the solid component is a solid nonionic surfactant, including a solid polyethylene glycol fatty alcohol ethers having the general formula $R(OCH2CH2)_nOH$, where R represents an alkyl group or a blend of alkyl groups, with for example 8 to 30 or 12 to 22 carbon atoms, and n is the degree of ethoxylation, e.g. 2 to 200. It may be that the lotion composition comprises from 20% to 80% by weight, or 30% to 70% by weight, or 40% to 60% by weight of this liquid polyethylene glycol, for example 50% by weight of Steareth-100.

Particulate Material

In one embodiment, the lotion composition additionally comprises at least one particulate material for further reducing the adherence of feces or menses to the skin. The particulate material includes the particles or beads described above as helping to reduce adherence to the skin of bodily exudates.

The particulate material is particulate during application onto the absorbent article. The particulate material is also such that it remains particulate when in contact with the skin and/or when in contact with urine, menses or feces. Hence, the particulate material is water-insoluble and it has a melting temperature above the processing temperature of the lotion composition, as described above.

The particulate material may have any mean particle size between 1 nanometer to 2 mm, between 1 nanometer to 500 micrometers, between 0.1 micrometer to 2 mm, between 50 nanometers to 1 micrometer, or any range or individual value within any of the ranges set forth herein. The minimum mean particle size may be at least 0.1 micrometer or at least 1 micrometer, or at least 10 micrometers, or at least 20 micrometers, up to about 500 micrometers or in some embodiments up to about 100 micrometers, and further in other embodiments up to about 30 micrometers. In one embodiment, it may be that the lotion composition to be applied and/or the applied coating comprises particles whereof less than 25% of the particles have an equivalent diameter of greater than 100 microns. In another embodiment, it may be that the lotion composition to be applied and/or the applied coating comprises particles whereof less than 25% of the particles have an equivalent diameter of less than 5 microns. In yet another embodiment, it may be that the lotion composition to be applied and/or the applied coating comprises particles whereof less than 25% of the particles have an equivalent diameter of less than 100 microns.

The particle material may be present in the lotion composition at a level from 0.05% to 25% (by weight of the lotion composition), from 0.05% to 15%, from 0.05% to 5%, or from 0.1% to 25%, or from 0.25% to 20%, or from 0.5% to 10% or even up to 5% by weight.

Suitably, the particles may have a density between about 0.5 gram/cm$^3$ and about 2.5 gram/cm$^3$. The density may be between about 0.5 gram/cm$^3$ and about 2.0 gram/cm$^3$, or between 0.8 gram/cm$^3$ and about 1.5 gram/cm$^3$. In one embodiment, the density may be less than about 1 gram/cm$^3$ so as to minimize particle settling and the density is greater than about 0.8 gram/cm$^3$ so as to minimize particle floatation.

In one embodiment, the lotion composition may comprise inorganic particles, including alumina silicates, silicates, silicas, mica and/or talc. Clays may also be used. However, in the present invention it may be that the particulate material is an organic material. The particles may be a non-active and/or non-reactive material. The particles may be porous, or non-porous. The particles may have any shape, and they may have a smooth surface, and they may be spherical or plate-like particles. The particles may comprise a coating agent on their surface or part thereof, for example a surfactant to change its properties, e.g. hydrophilicity. The particles, in particular when they are olefinic, may include a melt-additive, which is added during the manufacturing of the particles.

Suitable materials include but are not limited to: polystyrene particles, polypropylene and/or polyethylene (co)polymer particles, polytetrafluoroethylene particles, polymethylsilsesquioxane particles, nylon particles. Suitable commercially available particulate materials include but are not limited to: polyethylene particles, available from Honeywell International of Morristown, N.J. under the trade name ACUMIST; polymethyl methacrylate particles (microspheres), available from KOBO of South Plainfield, N.J. as BPA; lactone cross polymer particles (microspheres), available from KOBO as BPD; nylon 12 particles (microspheres), available from KOBO as NYLON SP; polymethylsilsesquioxane particles (microspheres), available from KOBO as TOSPEARL; cellulose particles (microspheres), available from KOBO as CELLO-BEADS; polytetrafluoroethylene powders, available from Micro Powders, Inc. of Tarrytown, N.Y. as MICROSLIP; blends of natural wax and micronized polymers as are available form Micro Powders as MICRO-CARE and particles of a copolymer of vinylidene chloride, acrylonitrile and methylmethacrylate available as EXPAN-CEL from Expancel, Inc. of Duluth, Ga. Micronized waxes, such as are available from Micro Powders as MICROEASE may also be incorporated. Polyolefin particles (powders) as are available from Equistar Chemical Corp. Houston, Tex. as MICROTHENE may be used. MICROTHENE FN510-00 from Equistar may be used.

The lotion composition herein may also comprise a coloring agent, which may be a dye compound, such as known in the art, but including for example food colorants and food dyes. The coloring agent may be water-dispersible or oil-dispersible. It may be a water-soluble dye, such as commonly specified by dye manufacturers. The coloring agent may be present in the lotion compositions at a level of for example 0.5 ppm to 5% by weight of the composition, or for example from 1 ppm or 0.005% to 1% or to 0.5% by weight of the composition.

Examples of coloring agents include FD&C and D&C dyes, including:
  FD&C Blue No. 1 (CI 42090, CAS RN 3844-45-9)
  FD&C Yellow No. 5 (CI 19140, CAS RN 1934-21-0)
  D&C Yellow No. 7 (CI 45350, CAS RN 2321-07-5)
  D&C Green No. 6 (CI 61565, CAS RN 128-80-3)
  D&C Green No. 8 (CI 59040, CAS RN 6358-69-6)
  FD&C GREEN NO. 3 (C.I. 42053) CAS RN: 2353-45-9
  D&C GREEN NO. 5 (C.I. 61570) CAS RN: 4403-90-1
  (Such dyes are available from for example Sensient Technologies Corporation, 777 East Wisconsin Ave., Milwaukee, Wis. 53202-5304, USA.)

Surprisingly, when incorporated in the lotion compositions of the invention that are hydrophilic, and/or that comprise the above-described solid and liquid components, the coloring agent migrates into the absorbent article when the article is wetted with bodily exudates, signaling to the user or caretaker that the absorbent article may need changing. Moreover, the presence of the coloring agent in the lotion composition may accentuate the presence of the storage element described herein, in particular when such as colored lotion composition is present on the storage element.

Absorbent Articles

Figure 1:
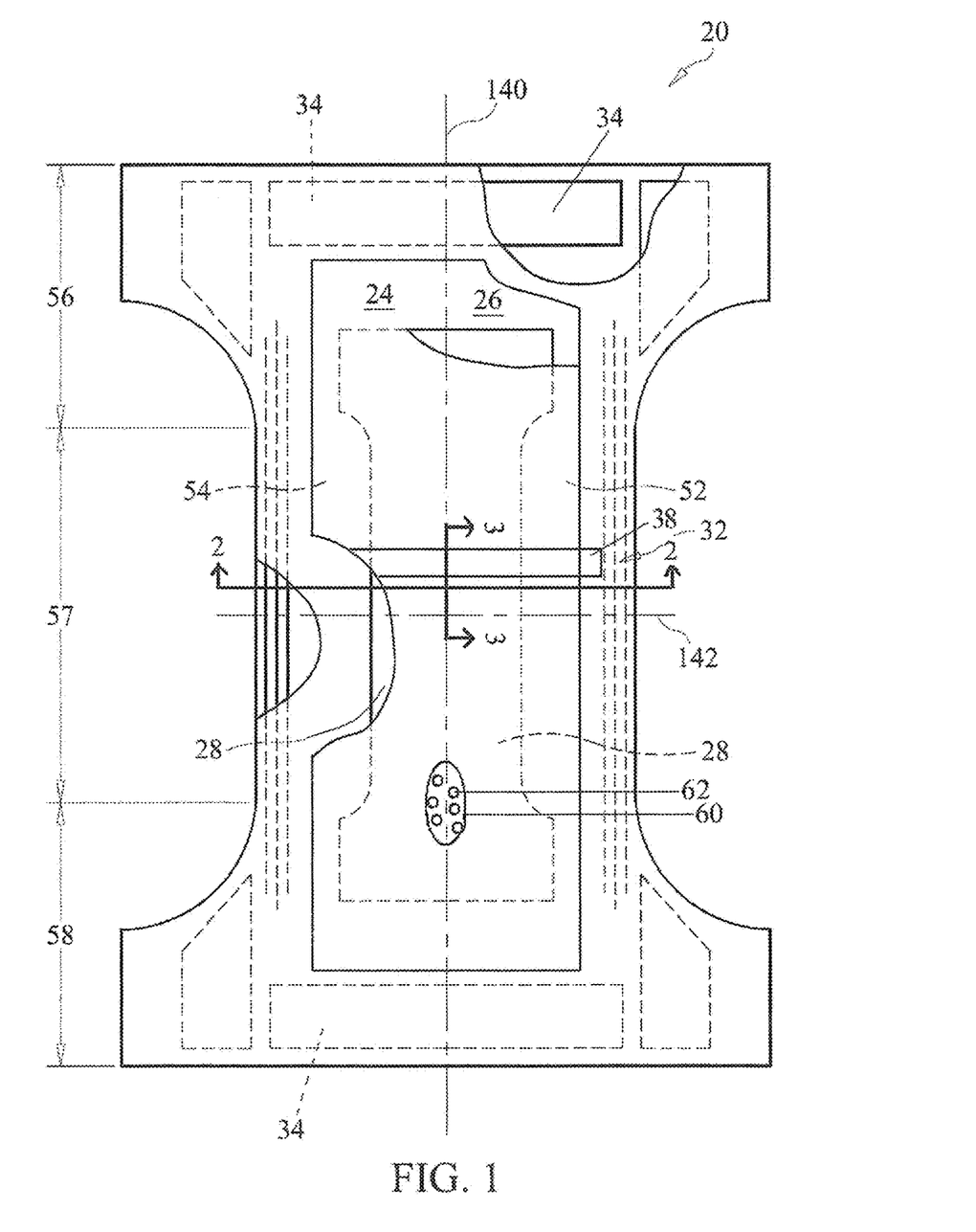
FIG. 1 is a plan view of an absorbent article in accordance with one non-limiting embodiment.

This invention relates to any absorbent articles such as such as diapers, adult incontinence articles, and feminine hygiene articles. These articles comprise for the purpose of the invention one or more components, comprising the lotion composition herein. This component may be the core coversheet, bodyside liner and/or the cuffs of the article, and/or the feces or Menses storage element or elements. FIG. 1 is a plan view of an absorbent article 20 in accordance with one non-limiting embodiment. The absorbent article 20 has portions cut away to reveal the underlying structure, the surface which will form the outer surface of the disposable garment is facing away from the viewer.

The absorbent article 20 herein has a longitudinal axis 140 and a transverse axis 142. The article 20 has further an inner, body facing surface 52 and an outer, garment facing surface 54 opposed to the inner surface 52.

One end portion of the article is configured as a front (waist) region 56 of the article 20. The opposite end portion is configured as a back (waist) region 58 of the article 20. A center portion 57 of the article, also referred to as a crotch region or portion, extends longitudinally between the front and back (waist) regions. The back (waist) portion 58, front (waist) portion 56 and the center portion or crotch portion 57 are each ⅓of the length of the article, for the purpose of this invention.

The absorbent article 20 herein typically comprises a backsheet 26 and an absorbent core 28 and a core coversheet or bodyside liner 24, wherein said absorbent 28 core may be a feces or menses storage element described herein. The backsheet 26 is typically liquid-impermeable. It may be air-permeable. It may be made of a variety of material, including nonwoven sheets and films, including laminates thereof. In one embodiment, the (liquid impermeable) backsheet 26 comprises a thin plastic film such as a thermoplastic film having a thickness of about 0.01 mm to about 0.05 mm. Suitable backsheet materials comprise typically breathable material, which permit vapors to escape from the absorbent article 20 while still preventing exudates from passing through the backsheet 26. Suitable backsheet films include those manufactured by Tredegar Industries Inc. of Terre Haute, Ind. and sold under the trade names X15306, X10962 and X10964. The backsheet, or any portion thereof, may be elastically extendable in one or more directions.

Materials for the core coversheet or bodyside liner 24 include woven sheets, nonwoven sheets, and films, including laminates thereof, and/or including apertured nonwovens and apertured films and apertured formed films, and including apertured formed thermoplastic films, apertured plastic films, and hydroformed thermoplastic films; but also including porous foams; reticulated foams; reticulated thermoplastic films; and thermoplastic scrims. Suitable woven and nonwoven materials can be made of natural fibers (e.g., wood or cotton fibers), synthetic fibers (e.g., polymeric fibers such as polyester, polypropylene, or polyethylene fibers) or from a combination of natural and synthetic fibers. Core coversheets or bodyside liners 24 that are or made of material(s) that are compliant, soft feeling, and non-irritating to the wearer's skin may be used. Further, the core coversheet or bodyside liner 24 may be liquid pervious permitting liquids,(e.g., urine) to readily penetrate through its thickness. It may be an apertured sheet. And said apertured sheets herein may have a plurality of apertures having an aperture size of at least about $0.2 mm^2$, but less than $2 cm^2$, or less than $1 cm^2$, or less than $0.5 cm^2$. Such an apertured sheet may have an open area of at least about 10%, the open area being the sum of the surface area of all apertures, on the surface faces the user in use.

The backsheet 26 may be directly or indirectly attached to or joined with for example the core coversheet or bodyside liner 24 and/or the barrier and/or leg cuffs 32 herein.

The absorbent core 28 generally is disposed between the core coversheet or bodyside liner 24 and the backsheet 26. The absorbent core 28 may comprise a multitude of layers, as described herein after. The absorbent core may comprise any absorbent material that is generally compressible, conformable, non-irritating to the wearer's skin, and capable of absorbing and retaining liquids such as urine and other certain body exudates.

The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles, some of which described in more detail below.

Further, the diapers herein may comprise a front and back waist band 34 and/or a fastening system, typically joined to the waistband 34, as known in the art. Fastening systems may comprise fastening tabs and landing zones, wherein the fastening tabs are attached or joined to the back region 58 of the diaper and the landing zones are part of the front region 56 of the diaper. A pants-type diaper may not have such fasteners, but it may have a back waist band and front waist and that are joined to form a continuous waistband.

Further suitable absorbent articles are disclosed e.g. in U.S. Pat. No. 6,482,191; U.S. Patent Application No. 2004/0092902 A; U.S. Patent Application No. 2004/0092900 A; U.S. Patent Application No. 2004/0162538 A; and U.S. Patent Application No. 2006/0058765 A.

Feces or Menses Storage Elements

The absorbent article herein comprises at least one feces or menses storage element. In one embodiment, the absorbent article is an infant diaper, or adult incontinence article, e.g. diaper, with a feces storage element. In another embodiment, the article is a feminine hygiene article, such as a sanitary napkin, with a menses storage element. In either embodiment, the article may comprise more than one such element.

In one embodiment, the absorbent article comprises as menses or feces storage element at least one pocket, or typically two pockets, formed by at least one pair of longitudinally extending cuffs, that are typically connected to one another, and which may be leg cuffs or may be barrier cuffs, as described below, typically being elasticated, as further described below. They may project out of plane of the article, having thus a z-direction height. The cuffs are typically connected to one another in the center portion of the article (center 33% of the length of the article), to thus have an X-shape, and to thus form a front and back pocket, to store the feces, or menses, in the back pocket. The cuffs may be made of a unitary sheet, being thus unitary cuffs, or they may be two separate cuffs that are joined to one another by an attachment means, including adhesive. In one embodiment, the feces or menses storage element is the absorbent core 28 comprising one or more holes.

Figure 2:
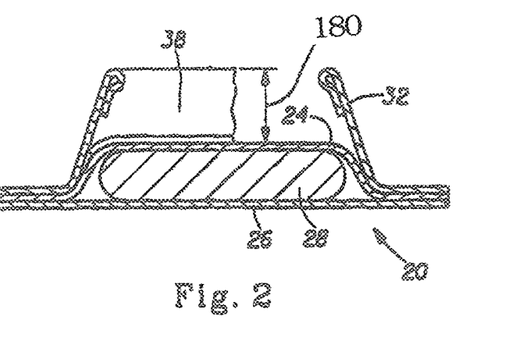
FIG. 2 is an offset vertical sectional view taken along line 2-2 of FIG. 1.
Figure 3:
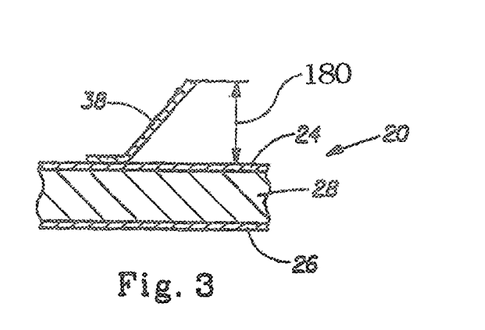
FIG. 3 is a fragmentary instant vertical sectional view taken along line 3-3 of FIG. 1.

In another embodiment, the absorbent article 20 comprises as menses or feces storage element at least one pair of longitudinally extending cuffs 32, which may be leg cuffs or may be barrier cuffs, having joined thereto a transverse barrier 38, also referred to as transverse partition. An example thereof is for example described in EP674499. The transverse barrier 38 serves to obstruct migration of feces from the front portion 56 to the back portion 58 of the article 20. The cuffs 32 and the transverse barrier 38 are typically upstanding from the plane of the article, e.g. from the plane of the backsheet 26 or absorbent core 28, in the in-use state of the article 20, having thus a certain z-direction dimension and height 180.

The transverse barrier 38 may be positioned substantially parallel to, or even coinciding with, the transverse center line 142 of the article in the center portion 57 of the absorbent article (the center portion being the portion having the center ⅓ of the length of the article, being positioned between the front and back portions of the article, which each have also ⅓ of the length of the article). The transverse barrier 38 may be a two-dimensional structure, like a sheet, having a length, substantially parallel to the transverse axis 142 of the article, and having a z-direction height; or a three-dimensional structure having a length and height as above, and having a width substantially parallel to the longitudinal axis 140 of the article. It may then be a T-shaped structure or sheet or for example a rectangular or square shaped component, placed between the cuffs 32 (of a pair of cuffs). The transverse barrier 38 may be unitary with said cuffs 32, in which case the cuffs 32 and transverse barrier structure 38 may for example have a unitary H-shape, or it may be attached to the cuffs as a separate component, by any attachment means, including adhesive.

The transverse barrier may be water-impermeable or urine-impermeable. The transverse barrier may be elasticated, in transverse direction and/or in longitudinal direction. The transverse barrier may be attached to the topsheet or absorbent core.

The transverse barrier may have the same average length, in transverse direction of the article, as the average distance between the cuffs at the point where the transverse barrier is present, e.g. the distance between the base lines of the cuffs, where the cuffs are attached to the backsheet or core or bodyside liner or core coversheet, or the transverse barrier may be wider or shorter than said distance between said cuffs.

The transverse barrier may have an effective height, as defined in EP674499, of at least 1 cm, or at least 1.5 cm, or at least 2 cm (average height). It may have an (average) absolute height measured at the point where it crosses the longitudinal center line, and measured between said point and the point where the transverse barrier connects to the underlying structure, e.g. the core coversheet or bodyside liner, of at least 1 cm, or at least 1.5 cm, or at least 2 cm.

The transverse barrier may have a longitudinal dimension, for example having a surface facing the user in use that has an average length dimension of at least 2 mm, or at least 5 mm, or at least 7 mm, and typically up to 5 cm, or up to 3 cm, or up to 2 cm.

The transverse barrier may be positioned under an angle with the plane of the article, for example concave towards the back of the article.

In either of the embodiments of the feces or menses storage elements above, each of the cuffs of a pair of cuffs is typically positioned along (and in close proximity or at) one longitudinal side of the article or of the absorbent core, for example a first (barrier) cuff positioned in longitudinal direction along a first longitudinal side edge of the absorbent article or of the absorbent core, when present, and a second (barrier) cuff positioned in longitudinal direction along a first longitudinal side edge of the absorbent article or of the absorbent core, when present. The longest longitudinal dimension, or length, of the cuff herein may be substantially parallel to the y-axis of the article. The cuffs are typically elasticated, for example comprising an elastic sheet material, and/or comprising one or more elastic strands that are attached to one or more sheet materials (for example a nonwoven). The average direction of stretch of the elasticated cuffs is typically parallel to the longitudinal direction of the article, e.g. the Y-axis. The width (i.e. in z-direction in use) and length of a cuff herein may vary, typically depending on the exact dimensions of the article, and the cuffs may span the whole length of the article, or only part thereof, but typically at least 50% of the length of the article, including the center portion of the article. The two cuffs of a pair may be mirror images of one another mirrored in the y-axis. The cuffs may be water- or urine-impermeable. Cuffs may be made of laminate nonwovens, comprising spunbond and meltblown layer(s), with thereto attached one or more elastic strands or elastic sheets.

Cuffs may have an average effective height, as defined above, or average absolute height, as defined above, of at least 1 cm, at least 1.5 cm, or at least 2 cm. Each cuff may have a variable height, for example being higher in the area where the transverse barrier is connected.

The cuff herein comprises typically at least one elastic material, such as a strand or string of elastic material, typically at least along the distal edge of the cuff that in use may contact the skin of the user.

In another embodiment, the absorbent article of the invention comprises as feces or menses storage element, a topsheet 24 with one or more openings 60 for the reception of feces or menses, and optionally for the reception of urine, said opening(s) 60 having in relaxed position (as defined herein) typically a total surface area (of all openings) of at least 4 cm$^2$ or at least 6 cm$^2$, or at least 10 cm$^2$ or even at least 15 cm$^2$. One or two openings 60 each may have such a surface area. In one embodiment, a single opening 60 may be in the form of a slit opening.

Said opening(s) lead to a void space underneath said topsheet, typically between the absorbent core and said topsheet, said void space being in use typically at least 1 cm$^3$, typically at least 2 cm$^3$, or at least 4 cm$^3$, or at least 6 cm$^3$ or at least 10 cm$^3$.

The opening(s) may be present in the center region and optionally in part of the front region of the topsheet (in use towards the front of the user) and in part of the back region of the topsheet. The topsheet may have a slit opening, which has a longitudinal dimension (length) substantially parallel to the longitudinal axis of the topsheet and of the diaper. In the stretched state, the opening (or openings) of the topsheet may be configured such that from 20% to 40%, or from 20% to 30% of the length of the opening (or total length of the openings) extends from the transverse axis of the topsheet towards the front edge of the topsheet, and the remaining percentage extends towards the back edge of the topsheet.

The dimensions and exact shape of the opening(s) may vary, depending on the size of the topsheet and/or the absorbent article. For example, in one embodiment the opening is in the form of a slit opening with substantially parallel, opposing, longitudinal side edges, which are connected in the front and back by for example a V-shaped or rounded V-shaped front edges and back edges, wherein both the front and back V-shaped edges comprise two angled edges, i.e. a hexagonal shape. In one embodiment, the front V-shaped edges have a larger angle with than the back V-shaped edges. The front V-shaped edges may have an angle of 20° to 140°, from 45° to 65°, or from 55° to 60°.

The maximum length of the (slit) opening(s) may be, for example, 40% to 90% or 50% to 80%, or about 60% to 70%, of the total length L of the absorbent article (in stretched state).

The average width of the opening(s) herein, in stretched state, may be from 5% to 30%, or 10% to 25%, of the average width of the topsheet (including opening width), or for example for a size 4 diaper, 15 mm to 60 mm, or from 20 mm to 40 mm.

The absorbent article with the topsheet with one or more openings may also comprise a transverse barrier, as described above, connected to said topsheet, e.g. between the opposing longitudinal edged of an opening, and/or connected to a pair of cuffs, as described above, that may be comprised by said article in addition to said topsheet with one or more openings.

In the embodiment of the invention, relating to an absorbent article with a topsheet with one or more openings, as referred to above, the topsheet has, typically adjacent to, or in close proximity with, and along each longitudinal side edge of the opening(s) an elasticated area, comprising elastic material, to form typically a pair of opposing, at least partially parallel, elasticated areas, such as described in copending application EP-A-1201212. The topsheet and/or the elasticated area may be an elastic sheet or it may be a formed from a sheet, such as a nonwoven, and thereto attached one or more elastic strands.

The elasticated areas may extend from said side edges of the opening(s) towards or completely to the front and back edge of the topsheet. The elasticated areas may be longer than the opening. The elasticated areas may be positioned over at least the part of the topsheet which in use is intended to receive body exudates, typically the topsheet minus the parts thereof which form (part of) the waist bands.

The width of the elasticated areas on the topsheet will vary, typically depending on the exact dimensions of the topsheet and/or the article.

For example, for size 4 diapers, an elasticated area, in stretched state, may be an elastic band, or a multitude of elastic strings, that has an average width of about 3 mm to 50 mm, 3 mm to 40 mm, or 3 mm, or 5 mm to 20 mm. Also, the length of the elasticated area will typically depend on the size of the topsheet and/or the article. For example, for a size 4 diaper, the average length of the elasticated area in stretched state, may be at least 35 cm, or from 35 cm to 45 cm.

The front end portions of two opposing elasticated areas may bend away from one another (in the plane of the topsheet), so that the distance between the end edges of the opposing front end portions of two opposing elastic areas is larger that the distance between the center portions of two opposing elastic areas, and equally, the distance between the end edges of the opposing back end portions of two opposing elastic areas is larger that the distance between the center portions of two opposing elastic area. Then, the front end portion of an elasticated area has typically an angle with a longitudinal line through the center portion of the elasticated area and parallel to the longitudinal axis of the topsheet, said angle being between 10° and 40°, or between 17° to 35°, or between 20° and 35°.

Then, the back end portion of each of the elasticated area may have also an angle with a longitudinal line through the center portion of the elasticated area and parallel to the longitudinal axis of the topsheet, said angle being between 10° and 40°, or between 17° to 35°, or between 20° and 35°. When both front end portions and both back end portions have an angle as above, then the primary elasticated areas have, as is herein referred to, an X-shape.

It may be that the front end and/or the back end and/or the center portion of an elasticated area are curved rather than straight, and then the angles above are determined by the angle of the tangent line through the center point of the front end and/or back end, with the line parallel to the longitudinal axis of the topsheet and tangent to the center point of the center portion of the elasticated area.

The topsheet may comprise further elasticated areas, either providing transverse or longitudinal elastic forces to the topsheet.

Elasticated areas herein may be formed by attaching an elasticated material in stretched state or partially being in stretched state to the topsheet material, e.g. nonwoven or nonwoven laminate, or to one or more carrier material(s), which is (are) then subsequently attached to the topsheet material.

The elastic materials are typically in the form of a multitude of strands or a single band with an average thickness (e.g. gauge) of at least 20 microns, at least 40 microns, or even at least 60 microns, up to about 300 microns, or even up to 200 microns or even up to 150 microns. Materials may have an average thickness of about 70 to 100 microns.

Elastic materials used hereto may include VFE-CD, available from Tredegar, and L-86, L-89, or L-90, available from Fulflex (Limerick, Ireland).

The longitudinal side edges of the topsheet herein may be connected, e.g. attached to, the longitudinal side edges of the absorbent core or of the backsheet (by any attachment means known in the art) to form longitudinal opposing attachment areas. In one embodiment of the present invention, the topsheet and the backsheet are attached directly to one another in some locations and are indirectly joined together in other locations.

The average width of the topsheet, including the width of the opening, may be larger than the average distance between the longitudinal attachment areas of the topsheet to the backsheet, mentioned above. Also it may be that the average width of the topsheet, including the width of the opening, is larger than the average width of the backsheet. The topsheet may for example have one or more transverse and/or, longitudinal folds, which can unfold in use and allow sagging of the core and backsheet, while the topsheet remains in place.

It may be that the topsheet is at least partially water- or urine-impermeable. In one embodiment, the topsheet or at least more than 50% of its surface area (that faces the wearer in use) is hydrophobic. Thereto, the topsheet may, for example, be made of a material having a Strike Through time for the first gush of more than 120 seconds, as determined by the test method described in co-pending application US2005/0095942A1 and US2006/0058766A1. Topsheets herein may be considered urine-impermeable and/or feces impermeable and thus suitable herein, when they have a low surface energy and a uniform pore size distribution, including with the low surface energy values, pore sizes and air permeability values described in co-pending application EP-A-1417945. Materials may be used with an alcohol repellency of at least 7 or at least 8 or at least 9, or at least 10; and may have a surface energy of less than 25 mN/m; and may have a contact angle with water of above 130°; and may have a mean pore size of less than 20 microns, less than 17 microns, or less than 13 microns, but may be at least 2 microns, or at least 5 microns. The topsheet may an air permeability of at least 3 Darcy, or at least 10 Darcy, or at least 20 Darcy, or at least 30 Darcy, or at least 50 Darcy.

A suitable topsheet may be manufactured from a wide range of materials, including woven or non-woven webs of natural fibers (e.g., wood or cotton fibers) or synthetic fibers (e.g., polyester, polyethylene and/or polypropylene fibers), or a combination of natural and synthetic fibers. If the topsheet includes fibers, the fibers may be for example spun bond, carded, wet-laid, melt blown, hydro entangled, or otherwise processed as is known in the art. Materials may be used that are compliant, soft feeling, and non-irritating to the wearer's skin.

Cuffs, topsheets and transverse barriers as described herein above may be made of laminate web materials comprising one on or more spunbond layers (S) and one or more meltblown layer(s) (M), whereby it may be that one, or both surfaces of the web materials are formed by spunbond layer(s). Such webs (sheets) may be used with a relatively high basis weight, for example more than 17 gram/m$^2$ (gsm) or more than 25 gsm, for example 34 gsm SMMS (whereby 12 gsm meltblown and 5 gsm spunbond); 34 gsm SMMS (whereby 10 gsm meltblown and 7 gsm spunbond); 30 gsm SMMS (whereby 10 gsm meltblown and 5 gsm spunbond); 30 gsm SMMS (whereby 8 gsm meltblown and 7 gsm spunbond); 34 gsm SMS (whereby 20 gsm meltblown and 7 gsm spunbond), or for example webs comprising two layers of 17 gsm SMMS, described above.

The menses or feces storage element may also be a three dimensional layer comprising one or more three dimensional hole(s) 62, including blind hole(s) and through hole(s).

This layer may be part of a multilayer absorbent core 28, such as an acquisition layer, capable to acquire liquid (menses/urine) and temporarily hold the liquid and allow it to pass through the acquisition layer to the storage layer underneath (in Z-direction), and/or a distribution layer that distributes it in the X and Y direction of the distribution layer, or a acquisition/distribution layer that serves both purposes. Then, the hole(s) 62 are capable to store the menses or feces, whilst the areas of the layer where no holes are present can acquire and/or distribute liquid. These types of layers typically do not serve to hold or store fluid (urine) for a longer period or permanently, but they facilitate the absorption of the fluid by the storage layer below.

The absorbent core 28 may also comprise a distribution layer and an acquisition layer, which both may comprise said holes 62.

The acquisition layer and/or distribution layer may be hydrophilic. It may comprise a fibrous three dimensional layer, and it may comprise two layers or more that are fibrous layers.

Acquisition layers may comprise partially bonded or unbonded polypropylene (PP) and/or polyester fibres, or polyethylene teraphthalate (PET) fibres. Alternatively, or in addition, it may be that the acquisition layer comprises modified (cellulose) fibers, including chemically stiffened, twisted and/or curled (curly) (cellulose) fibres, including chemically stiffened, twisted and/or curled crosslinked cellulose or synthetic polymer fibres (including such cellulose fibres). Materials may be used that are available from Weyerhaeuser under as CMC520 and CMC517. Also it may be that the acquisition layer comprises a multitude of bonded, carded bonded nonwoven layers, such as carded resin-bonded nonwovens, embossed carded resin-bonded nonwoven acquisition layers, and optionally highloft carded resin-bonded nonwoven acquisition layers, or carded through-air-bonded nonwoven acquisition layers, carded thermo-bonded nonwoven acquisition layers; non-embossed carded resin-bonded non-woven acquisition layers may be used. Materials may be used with a high basis weight, i.e. of 40 gsm or more, or even 60 gsm or more. Materials as above that may be used herein are available from BBA Fiberweb/Tenotex (Italy) under the trade name Printex AQL1 Phil (43 gsm, white); or from Freudenberg/Halifax under the code AL 1060 (SC V and SO, and AR10) and under the code 114/011/05 (typically 43 or 60 gsm); or from Lohmann, under the trade name Paraprint.

Two or more acquisition layers may be used, whereby one or each may comprise one or more holes.

The storage layer of the absorbent core typically comprises water-swellable polymeric particulate material, also referred to as water-absorbing polymer material, or absorbent gelling material (AGM). It may comprise one or more holes, as described herein after. It may be that the storage layer comprises hole(s), but the overlying distribution layer and/or acquisition layer and/or core coversheet does not comprise hole(s), but said layer(s) and/or core cover sheet undulates into the one or more holes of the storage layer, so that the hole(s) still remain void for feces or menses storage. Alternatively, the acquisition layer and/or distribution layer and/or core coversheet may each comprise one or more holes that coincide with one or more, so that one or more or typically all of the holes in the storage layer and one or more or typically all of the hole(s) in the acquisition layer and/or distribution layer, and optionally the core coversheet, form the hole(s) as referred to herein.

In one embodiment, the absorbent core comprises a core coversheet that does not comprise any holes, but that undulates into the one or more holes in the underlying acquisition layer and/or distribution layer or in the hole(s) of the acquisition layer and/or distribution layer and into the coinciding hole(s) of the storage layer.

The hole or holes herein, including through holes and/or blind holes, are capable to store and immobilize feces. When the holes are blind holes, it may be that the holes have an average depth or caliper that is about 50% to 95% of the average thickness or caliper of the layer or layers comprising said holes. In one embodiment, the storage layer comprises one or more holes that are blind holes, so a certain amount of water-swellable polymeric particulate material is present under the blind hole(s).

The hole or holes herein may have any shape and also the circumferences of the hole or holes may have any shape, including round or oval, square or rectangular. The holes may be cylindrical, cone-shaped, cubical, and channel-shaped. The hole(s) herein may (each) have a smallest dimension in the plane of the article (Y or X direction) of at least 3 mm, or of at least 4 mm, or of at least 5 mm, or even at least 10 mm.

The hole(s) may have each a depth or caliper of for example at least 0.5 mm, or at least 1 mm or at least 1.3 mm or at least 1.5 mm, and the maximum depth will depend on the caliper of the layer comprising the hole(s).

The maximum dimension of each hole in the plane of the article may depends on the number of holes present, the size of the article, and quantity of menses or feces envisaged to be stored.

For example, for infant diapers, the total surface area of the hole or the total surface area of all the holes (in an in-use situation; measured in the plane of the article where the circumferential edge of the opening is closest to the user in use) is at least 3 $cm^2$, or at least 5 $cm^2$ or at least 7 $cm^2$; for adult incontinence articles, the total surface area of the hole or the total surface area of all the holes (as measured above) may for example be at least 5 $cm^2$, or at least 7 $cm^2$ or at least 10 $cm^2$; for feminine hygiene article, the total surface area of the hole or the total surface area of all the holes (as measured above) may for example be at least 1 $cm^2$, or at least 2 $cm^2$ or at least 3 $cm^3$.

Typically, for infant diapers, the total volume of the hole or the total volume of all the holes (in an in-use situation) is at least 0.5 $cm^3$, or at least 1 $cm^3$ or at least 2 $cm^3$. Typically, for adult incontinence articles, the total volume of the hole or the total volume of all the holes (in an in-use situation) is at least 1 $cm^3$, or at least 2 $cm^3$ or at least 3 $cm^3$. Typically, for feminine hygiene article, the total volume of the hole or the total volume of all the holes (in an in-use situation) is at least 0.2 $cm^3$, or at least 0.3 $cm^3$ or at least 0.5 $cm^3$.

In one embodiment, the absorbent article comprises an absorbent core with said hole or holes only in the back half thereof (back 50% of the length of the absorbent core).

In one embodiment herein, the storage layer and optionally the acquisition layer and/or distribution layer comprises one or two or three or four holes, and each having a smallest dimension in the plane of the article of at least 1 cm or even at least 2 cm or even at least 3 cm. In one embodiment, only one hole is present in the absorbent core, e.g. the storage layer and optionally in the acquisition layer and/or distribution layer, said hole having a smallest dimension of at least 2 cm, or at least 3 cm, or at least 4 cm.

In one embodiment the layer or layers with one or more holes are such that the layer or layers have an open surface area (measured on the surface area of the layer closest to the user in use) from 10% to 50%, or even from 10% to 45% or from 10% to 40%, of the total surface area of said layer (i.e. whereby the open surface area is the sum of the surface areas of the holes as measured in the cross section of the holes in or on the surface layer closest to the wearer in use).

In one embodiment, it may be that the core cover sheet does not comprise holes as defined above, so that the material of the layers with hole(s) is not exposed to the skin of the user.

In one embodiment herein, the absorbent article comprises in addition to the absorbent core with one or more holes, a topsheet (as described above) with one or more opening, leading to a void space between said topsheet and the underlying absorbent core with one or more holes, so that the feces or menses can be effectively stored in said void space and in said hole or holes. In another embodiment herein, the absorbent article comprises in addition to the absorbent core with one or more holes, cuffs that are connected to one another in the center region, as described above, forming thereby one or more pockets, so that the feces or menses can be effectively stored in said pocket(s) defined by said cuffs and in addition, in said hole or holes.

In another embodiment herein, the absorbent article comprises in addition to the absorbent core with one or more holes, and a transverse barrier, connected to for example a pair of cuffs, as described above. The hole or holes may than be present in at least the back portion of the article; the transverse barrier may than be positioned typically in close proximity to the transverse center line of the article, so that the feces can be effectively stored in said hole or holes and said transverse barrier will ensure feces is stored away from the genitals.

The absorbent article comprises the lotion composition herein typically on, or in, a component that is use contact the user's skin, such as the cuffs, topsheet, core coversheet or bodyside liner.

In one embodiment herein, the lotion composition is present on the feces or menses storage element. In one embodiment, it is present on an elasticated area or portion of such a storage element.

Surprisingly, the inventors found that the (hydrophilic) lotion compositions herein, unlike the hydrophobic lotions known in the art, are compatible with the elastic materials that may be present in the feces or menses storage element of the absorbent articles, such as the cuffs, the elasticated topsheet with one or more openings, or the elasticated transverse barrier.

For example, the topsheet with the opening(s) as described above may comprise said lotion compositions herein for example on, or only on, the areas along the edges of the opening(s), that may comprise in addition elastic material.

The lotion composition may alternatively or in addition be present on the cuffs, as described above, or part thereof.

The lotion composition herein may alternatively or in addition be present on the transverse barrier, described above, or part thereof.

When the absorbent core comprises one or more holes, the lotion composition herein may be present at least in close proximity of the edges of the hole(s) and may be present in the holes, or part thereof. In one embodiment, at least part of the core coversheet that covers and undulates into the holes comprises said lotion composition.

A component or feces or menses storage element of the articles herein may comprise over its entire surface said lotion composition, or only on a portion or portions thereof. Typically, at least a total surface area (measured on the surface facing the user in use) of at least 1 cm², at least 4 cm² or in some embodiments even at least 10 cm² or at least 15 cm² comprises said lotion composition; and thus, in one embodiment, the topsheet with opening(s), and/or the absorbent core, e.g. the core coversheet thereof, and/or the cuffs comprises said lotion composition such that the total area of said element with lotion composition thereon is at least 1 cm², at least 4 cm² or at least 10 cm² or at least 15 cm², or for example at least 30 cm² or at least 50 cm²; and in certain embodiments the core cover or topsheet comprises said lotion composition on a surface area of for example at least 70 cm² and for example up to 100 cm².

The lotion composition may be applied in any single shape or pattern, including a square or rectangular, round, oval; or figurative shape or a pattern of shapes, including rectangular shapes like a multitude of stripes, or including a multitude of squares, or dots or oval shapes, or even figurative figures.

The pattern in which the lotion composition may be applied and/or the amount of lotion composition applied can be the same for the rear third of the article (i.e. a third of the longitudinal extension of the absorbent articles starting from the outer edge of the chassis in the rear waist region), the central third of the article and the front third of the article. Alternatively, the pattern, in which the lotion composition is applied and/or the amount of lotion composition applied can be different for the rear, central and front third of the article. As the lotion composition of the present invention has anti-stick properties, it may be comprised in those regions of the absorbent articles, which lie adjacent the skin areas of the wearer, which typically are contaminated with menses or feces. Thus, the lotion composition should at least be comprised in those regions of the articles, which lie adjacent the buttocks and the whole groove length of the wearer in use, and/or in the region of the genitals.

If the lotion composition is applied in the form of longitudinal stripes, the stripes may extend into the rear waist region of the absorbent article to the extent that they also cover the buttocks and most of the groove length. Also, the number or the density of the stripes may be higher in those areas lying against the areas typically affected with feces smeared against the skin, e.g. the back half of the article. Further, the basis weight of the stripes may be higher in those areas lying against the areas typically affected with feces smeared against the skin. If the lotion composition is applied in the form of figures, like dots, the density of the figures (e.g. dots density, dots being closer together) and/or the size of the figures and/or the basis weight of the lotion composition comprised by the figures may be higher in those areas lying against the areas typically affected with feces smeared against the skin.

Test Methods

Water Solubility

Water solubility of the lotion composition or any compound used to formulate the lotion composition is determined as follows: 100 mg starting amount (SA) of the lotion composition is applied to a glass slide (2.5 cm×8 cm) of known weight, such that the lotion covers an area of 2.5 cm×5 cm on the glass slide. The slide is then placed flat in a beaker containing 75 ml of deionized water at 20° C. The water with the lotion composition therein is not stirred. After 4 hours the glass slide is removed from the beaker and put in an oven at 60° C., 0% RH (relative humidity) to remove the water. After drying it is weighted to determine the residual amount of lotion composition on the slide. The lotion composition of the present invention is water soluble if residual amount (RA) of lotion composition on the plate after drying is below 60%, below 20% and even below 10% (of the 100 mg that have been applied to the glass slide). These values correspond to a water solubility of at least 40%, at least 80% and at least 90% which is determined as follows:

$$[(SA-RA)]/SA \times 100\% = \text{water solubility(in \%)}$$

Such lotion compositions having relatively good water solubility are considered to be hydrophilic within the meaning of the present invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article to be worn by a wearer against the skin comprising a backsheet; a feces or menses storage element comprising at least one pair of longitudinally extending cuffs having joined thereto a transverse barrier, the cuffs and the transverse barrier upstanding from a plane of the backsheet, the transverse barrier having thus an average z-direction height of at least 1 cm; and a hydrophilic lotion composition having a water solubility of at least 40%, wherein the hydrophilic lotion composition comprises:
   25% to 75% by weight of a first component which is liquid at 25° C., the first component comprising one or more compounds selected from the group consisting of liquid nonionic surfactants having an HLB value greater than or equal to 10, liquid polyhydric alcoholic solvents, and liquid fatty acid esters comprising at least one fatty acid unit and at least one (poly) ethylene glycol unit and/or (poly) propylene glycol unit; and
   25% to 75% by weight of a second component which is solid at 25° C., the second component comprising one or more compounds selected from the group consisting of solid polypropylene glycols, solid polypropylene glycol derivatives, solid ethoxylated natural oils, solid ethoxylated natural fats, solid propoxylated natural oils, and solid propoxylated natural fats;
   wherein the lotion composition comprises a coloring agent comprising a water-soluble dye;
   wherein the absorbent article comprises a core cover sheet, and wherein the lotion composition is applied to the feces or menses storage element and to the core coversheet.

2. An absorbent article to be worn by a wearer against the skin comprising:
   a backsheet; and
   a feces or menses storage element, the storage element comprising:
      at least one pair of longitudinally extending cuffs having joined thereto a transverse barrier, the cuffs and the transverse barrier upstanding from a plane of the backsheet, the transverse barrier having thus an average z-direction height of at least 1 cm;
   a wearer's skin-faceable surface; and
   a lotion composition, the lotion composition comprising:
      25% to 75% by weight of a first component which is liquid at 25° C.; and
      25% to 75% by weight of a second component which is solid at 25° C.;
   wherein the first component comprises one or more compounds selected from the group consisting of:
      (a) liquid nonionic surfactants having an HLB value greater than or equal to 10; and
      (b) liquid fatty acid esters comprising at least one fatty acid unit and at least one (poly) ethylene glycol unit and/or (poly) propylene glycol unit;
   wherein the second component comprises one or more compounds selected from the group consisting of:
      (c) solid polyethylene glycols, solid polypropylene glycols, solid polyethylene glycol derivatives, or solid polypropylene glycol derivatives;
      (d) solid nonionic surfactants with HLB value of at least 10;
      (e) solid fatty compounds selected from the group consisting of solid fatty acids, solid fatty soaps, and solid fatty alcohols; and
      (f) solid ethoxylated natural oils and fats and propoxylated natural oils and fats;
   wherein the lotion composition comprises a coloring agent comprising a water-soluble dye;
   wherein the absorbent article comprises a core cover sheet, and wherein the lotion composition is applied to the feces or menses storage element and to the core coversheet.

3. The absorbent article of claim 2, wherein the lotion composition has a water solubility of at least 30%.

4. The absorbent article of claim 1, wherein the feces or menses storage element comprises an absorbent core comprising one or more holes.

5. The absorbent article of claim 1, wherein the article comprises an absorbent core and wherein the feces or menses storage element comprises a topsheet and a void space defined between the core and the topsheet, wherein the topsheet comprises one or more openings leading to the void space, and wherein the opening or openings have a surface area of at least 4 cm² (in relaxed position).

6. The absorbent article of claim 5, wherein the topsheet comprises one or more elasticated areas, wherein the one or more openings have longitudinal side edges, and wherein the one or more elasticated areas are present along at least a portion of the longitudinal side edges of the one or more openings.

7. The absorbent article of claim 1, wherein the article comprises a core coversheet and wherein the feces or menses storage element and/or the core cover sheet has one or more first areas comprising the lotion composition and one or more second areas not comprising the lotion composition, and wherein the first area comprises elastic material.

8. The absorbent article of claim 2 wherein the first component comprises a liquid fatty acid ester comprising at least one fatty acid unit and at least one ethylene glycol unit and the second component comprises a solid polypropylene glycol.

9. The absorbent article of claim 1, wherein the absorbent article is an adult incontinence article or infant diaper.

* * * * *